(12) United States Patent
Zaidi

(10) Patent No.: US 7,084,966 B2
(45) Date of Patent: Aug. 1, 2006

(54) OPTICAL MEASUREMENT OF DEVICE FEATURES USING LENSLET ARRAY ILLUMINATION

(75) Inventor: Syed Shoaib Hasan Zaidi, Poughkeepsie, NY (US)

(73) Assignee: Infineon Technologies AG, Munich (DE)

( * ) Notice: Subject to any disclaimer, the term of this patent is extended or adjusted under 35 U.S.C. 154(b) by 317 days.

(21) Appl. No.: 10/689,241

(22) Filed: Oct. 20, 2003

(65) Prior Publication Data

US 2005/0083514 A1    Apr. 21, 2005

(51) Int. Cl.
G01N 21/00  (2006.01)

(52) U.S. Cl. .................. 356/237.2; 356/237.5

(58) Field of Classification Search .......... None
See application file for complete search history.

(56) References Cited

U.S. PATENT DOCUMENTS

| | | | |
|---|---|---|---|
| 5,248,876 A | 9/1993 | Kerstens et al. | |
| 5,415,835 A | 5/1995 | Brueck et al. | |
| 5,436,725 A | 7/1995 | Ledger | |
| 5,543,919 A * | 8/1996 | Mumola | 356/632 |
| 5,705,321 A | 1/1998 | Brueck et al. | |
| 5,759,744 A | 6/1998 | Brueck et al. | |
| RE36,113 E | 2/1999 | Brueck et al. | |
| 5,889,593 A * | 3/1999 | Bareket | 356/445 |
| 5,966,212 A * | 10/1999 | Hendler et al. | 356/239.3 |
| 6,042,998 A | 3/2000 | Brueck et al. | |
| 6,233,044 B1 | 5/2001 | Brueck et al. | |
| 6,248,988 B1 | 6/2001 | Krantz | |
| 6,320,648 B1 | 11/2001 | Brueck et al. | |
| 6,548,314 B1 | 4/2003 | Zaidi | |
| 6,596,377 B1 | 7/2003 | Hersee et al. | |
| 6,628,390 B1 | 9/2003 | Johnson | |
| 6,731,383 B1 * | 5/2004 | Watkins et al. | 356/237.2 |
| 2002/0088858 A1 | 7/2002 | Tanaami et al. | |
| 2002/0191178 A1 | 12/2002 | Watkins et al. | |
| 2003/0063278 A1 | 4/2003 | Zaidi | |
| 2003/0085335 A1 | 5/2003 | Almogy et al. | |
| 2003/0095251 A1 * | 5/2003 | Maeda et al. | 356/237.2 |
| 2003/0133127 A1 | 7/2003 | Zaidi et al. | |

FOREIGN PATENT DOCUMENTS

| | | |
|---|---|---|
| EP | 0 647 828 A2 | 4/1995 |
| EP | 1 223 421 A2 | 7/2002 |

OTHER PUBLICATIONS

Bogdanov, V., et al., "Parallel, confocol, and complete spectrum imager for fluorescent detection of high-density microarray," Part of the SPIE Conference on Multidimensional Spectroscopy: Acquisition, Interpretation, and Automation, Jan. 1999, pp. 298-307, vol. 3605.

(Continued)

*Primary Examiner*—Michael P. Stafira
(74) *Attorney, Agent, or Firm*—Slater & Matsil LLP

(57) ABSTRACT

The properties of features formed in a substrate are measured. Lenslet array illumination is used to illuminate regions of a substrate so that the features of interest occupy a greater proportion of the illuminated area. The signal-to-noise ratio of the measurement signal is therefore increased, and the sensitivity of the measurement is thus improved.

30 Claims, 4 Drawing Sheets

OTHER PUBLICATIONS

Sui, et al., "Integrated Process Control Using an In Situ Sensor for Etch," Solid State Technology, Apr. 2002.

Herrick, et al., "Using Broadband Reflectometry for Fast Trench-Depth Measurement," Solid State Technology, Feb. 2003.

Logofatu, "Tools for Testing—A Non-Contact, Nondestructive Option for Characterizing Lithography Test Samples, Scatterometry Performance Improves," Spie's OE Magazine, Aug. 2003, pp. 40-42.

McNeil, J.R., "Scatterometry Applied to Microelectronics Processing," IEEE Lasers and Electr-Optics Society Newsletter, vol. 14, No. 5, Oct. 2005, 3 pages.

Seiler, D.G., et al., "Challenges of Metrology and Characterization Measurements for ULSI Technology," R & D Institute for Photonics Engineering, Tokyo, Japan, Nov. 22, 2000, pp. 158-166.

"The Shack-Hartmann Sensor," Wave Front Sciences, http://www.polytec-pi.fr/wavefrontsciences/ophthalmic/hartmannsensor.html, Aug. 10, 2003, 2 pages.

"The Shak-Hartmann Sensor," Wave Front Sciences Optics and Instrumentation, www.wavefrontsciences.com/opthalmic/hartmannsensor.html, Aug. 19, 2003, 2 pages.

* cited by examiner

OPTICAL MEASUREMENT OF DEVICE FEATURES USING LENSLET ARRAY ILLUMINATION

BACKGROUND OF THE INVENTION

The present invention is directed to the fabrication of semiconductor devices and, more particularly, to the metrology of features formed during the fabrication of such semiconductor devices.

The manufacture of a semiconductor device typically requires a large number of process steps. Each process step includes one or more processing parameters that must be controlled within a relatively narrow range to obtain devices which have the desired characteristics and to obtain an acceptable yield of devices having such characteristics. In addition to controlling the conditions of each process step, the dimensions and structure of various features are determined throughout the fabrication process to ensure that the process conditions remain under control as well as to verify the calibration of various processing systems or tools. Such measurements may be carried out on control wafers, namely non-device wafers that are processed with the device wafers, or on the actual device wafers. Among the features or critical dimensions (CD) are line width, line height, sidewall angle and profile, and trench depth, as well as the presence of open or partially-opened contact windows or vias.

Advances in semiconductor processing materials and techniques have reduced the overall size of the device circuit elements or features while increasing the number of elements on a single chip. The decreased feature size and increased density have made the use of various metrology techniques more critical while also increasing the difficulty of obtaining accurate and repeatable measurements with these techniques. As an example, optical metrology systems typically use incident, scattered or reflected white or monochromatic light to illuminate the feature or structure where a measurement is taken. Such measurements are best taken, namely have the highest contrast, when the area of the feature to be measured is approximately equal to the background i.e., the remaining area that is illuminated. However, as the features of interest have become smaller, the area of these features may become a much smaller proportion of the total illuminated area and causes increased noise in the measurement signal, thereby reducing the sensitivity of the measurement.

Attempts to reduce the total illuminated area, so that the area of the features of interest is a greater proportion of the total illuminated area, include the use of improved lenses and/or the incorporation of apertures or pinholes. However, as the sizes of the features of interest further decrease, further reductions in the total illuminated area are needed.

It is therefore desirable to carry out such optical measurements in which the total illuminated area is further reduced with respect to the size of the features of interest.

SUMMARY OF THE INVENTION

The present invention incorporates illumination using lenslet arrays into the optical measurement system so that the size of the total illuminated area is reduced.

In accordance with an aspect of the invention, background illumination is minimized while illuminating features formed on a substrate. A light beam is directed onto a lenslet array comprised of at least two lenslets. The light beam is divided into at least two light rays and the light rays are directed onto the substrate using the lenslet array. The lenslets of the lenslet array each direct a respective one of the light rays onto a corresponding region of the substrate that includes a feature formed on the substrate. The width of the region and the width of the feature are substantially equal.

According to another aspect of the invention, background illumination is minimized while illuminating features formed on the substrate. A light beam is directed onto a lenslet array comprised of a plurality of lenslets. The beam is divided into a plurality of light rays and each of the light rays is directed onto the substrate using the lenslet array. The lenslet of the lenslet array each direct a respective one of the light rays onto a corresponding region of the substrate that includes a feature formed on the substrate. Adjacent lenslets of the lenslet array direct adjacent light rays onto adjacent features formed on the substrate.

According to a further aspect of the invention, a property of features formed on a substrate is measured. A light beam is directed onto a lenslet array comprised of at least two lenslets. The light beam is divided into at least two light rays and the light rays are directed onto the substrate using the lenslet array. A property of at least one feature is measured using light detected from the feature. The lenslets of the lenslet array each direct a respective one of the light rays onto a corresponding region of the substrate that includes the feature formed on the substrate.

In accordance with a still further aspect of the invention, an apparatus measures a property of features formed on a substrate. A lenslet array is comprised of at least two lenslets. The lenslets of the lenslet array divide an incident light beam into at least two light rays and each directs a respective one of the light rays onto a corresponding region of the substrate that includes a feature formed on the substrate. A detection system measures a property of the feature using light detected from the substrate.

The foregoing aspects, features, and advantages of the present invention will be further appreciated when considered with reference to the following description of the preferred embodiments and accompanying drawings.

DETAILED DESCRIPTION

Figure 1:
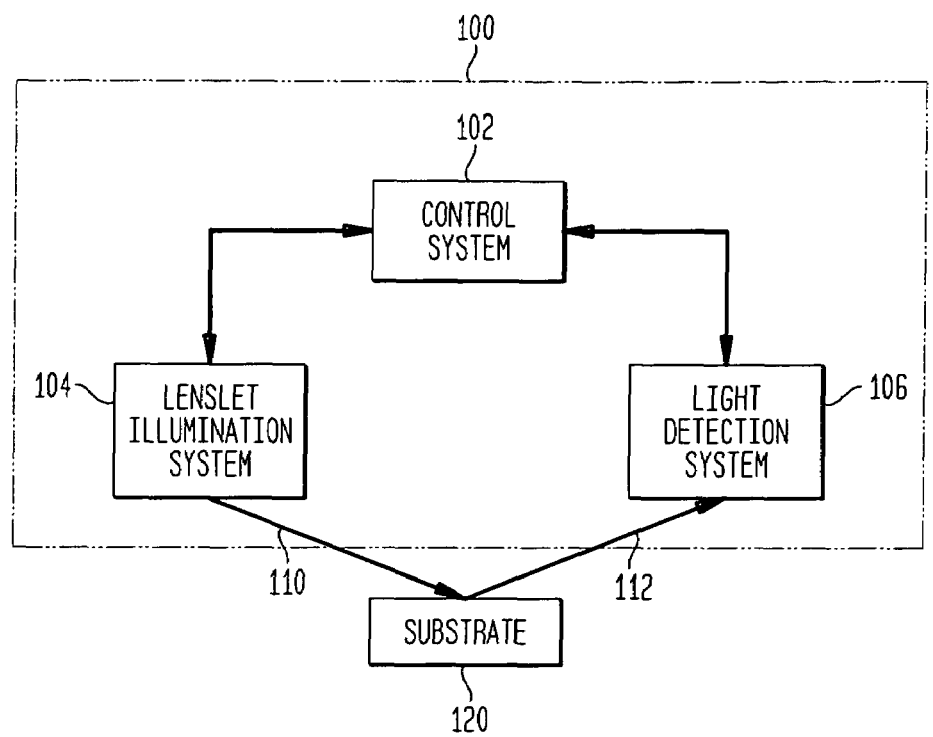
FIG. 1 is a diagram showing an example of a metrology apparatus in accordance with an aspect of the invention.

FIG. 1 illustrates a metrology system 100 of the invention that is used for obtaining data relating to the dimensions and/or structure of features formed on a substrate 120. The metrology system 100 includes a control system 102, a lenslet array illumination system 104, and a light detection system 106. The illumination system 104 generates incident light 110 onto the substrate 120. The incident light 110 is in the form of light rays generated by a lenslet array disposed within the illumination system 104. The illumination system 104 is configured such that each of the light rays illuminates a respective region of the substrate 120.

The light detection system 106 detects light 112 that is reflected or scattered off the surface of the substrate 120, generates measurement data relating to the detected light 112 and delivers the data to the control system 102. The control system 102 analyzes the data received from the light detection system 106 and delivers the data to a display (not shown) or to other output devices. Such light detection systems and control systems are known in the art and comprise part of existing metrology systems as are manufactured by KLA-Tencor Corp., Leica Microsystems Wetzlar Gmbh, FEI Company etc.

The control system may also deliver the data to another processor for further analysis or to a processing tool to control part of the fabrication process based on the data. The control system 102 also controls the illumination system 104, including the optical elements disposed therein, to ensure that the light rays illuminate the surface of the substrate 120 as well as to control the location of the regions illuminated. Further, when illumination of more than one region is desired, the control system 102 also controls the optics of the illumination system 104 to adjust the spacing and angle between the light rays so that they illuminate the desired regions on the substrate.

Figure 2:
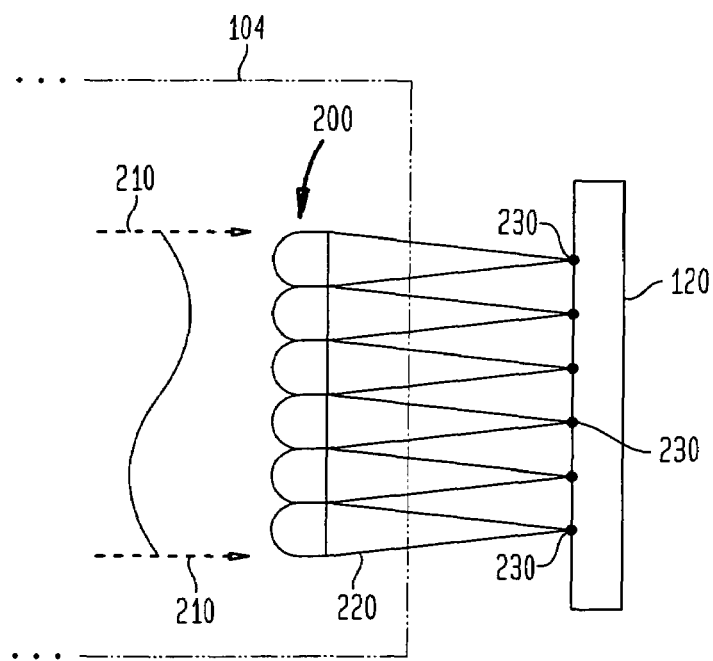
FIG. 2 is a diagram showing an example of a lenslet array that is incorporated into the apparatus of FIG. 1 in accordance with an aspect of the invention.

FIG. 2 illustrates an example of a lenslet array that forms part of the illumination system 104 in accordance with an embodiment of the invention. A light source (not shown) generates a light beam 210 that impinges upon a lenslet array 200. The array 200 divides the light beam 210 into a plurality of light rays 220 and directs the light rays onto a surface of the substrate 220 at respective locations 230. The lenslet array 200 divides the incoming light 210 into a plurality of sub-apertures, each having a corresponding resolution.

Preferably, the focal plane of the lenslet array 200 is coincident with the surface of the substrate 120. However, the lenslet array 200 may alternatively be oriented such that its focal plane is slightly above or below the surface of substrate 120 to adjust the size of the regions illuminated at the locations 230.

The lenslet array is comprised of a two-dimensional array of microscopic lenses each having a diameter of between 100 to 200 microns. The techniques for manufacturing such lenslet arrays is known in the art and typically uses processing techniques similar to those used in the manufacture of integrated circuit devices.

The arrangement shown in FIG. 2 directs the light rays 220 onto the surface of the substrate 120 at a direction normal to the surface. Alternatively, the light rays may be directed on the surface at an oblique angle, as shown in FIGS. 3 and 4.

Figure 3:
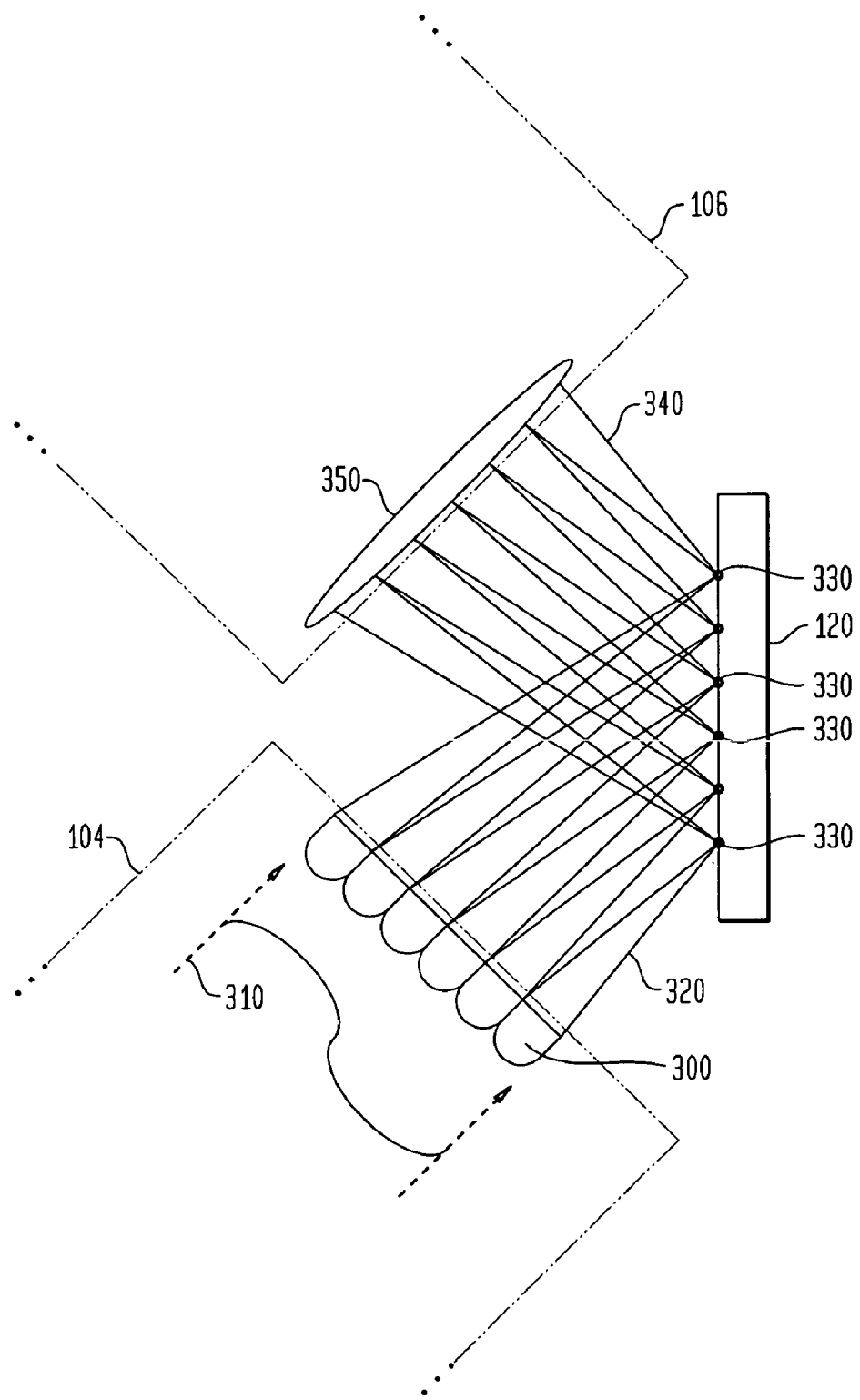
FIG. 3 is a diagram showing an example of a lenslet array that is incorporated into the apparatus of FIG. 1 in accordance with a further aspect of the invention.

FIG. 3 shows an arrangement in which the illumination system 104 includes a lenslet array 300 that directs incoming light 310 from a light source (not shown) and forms a plurality of light rays 320 onto a plurality of locations 330 on the surface of the substrate 120. The light rays are then reflected or scattered off the surface of the substrate and form a plurality of further light rays 340 which are directed into the light detection system 106 where they are focused by a lens 350 for further measurement in a known manner.

Figure 4:
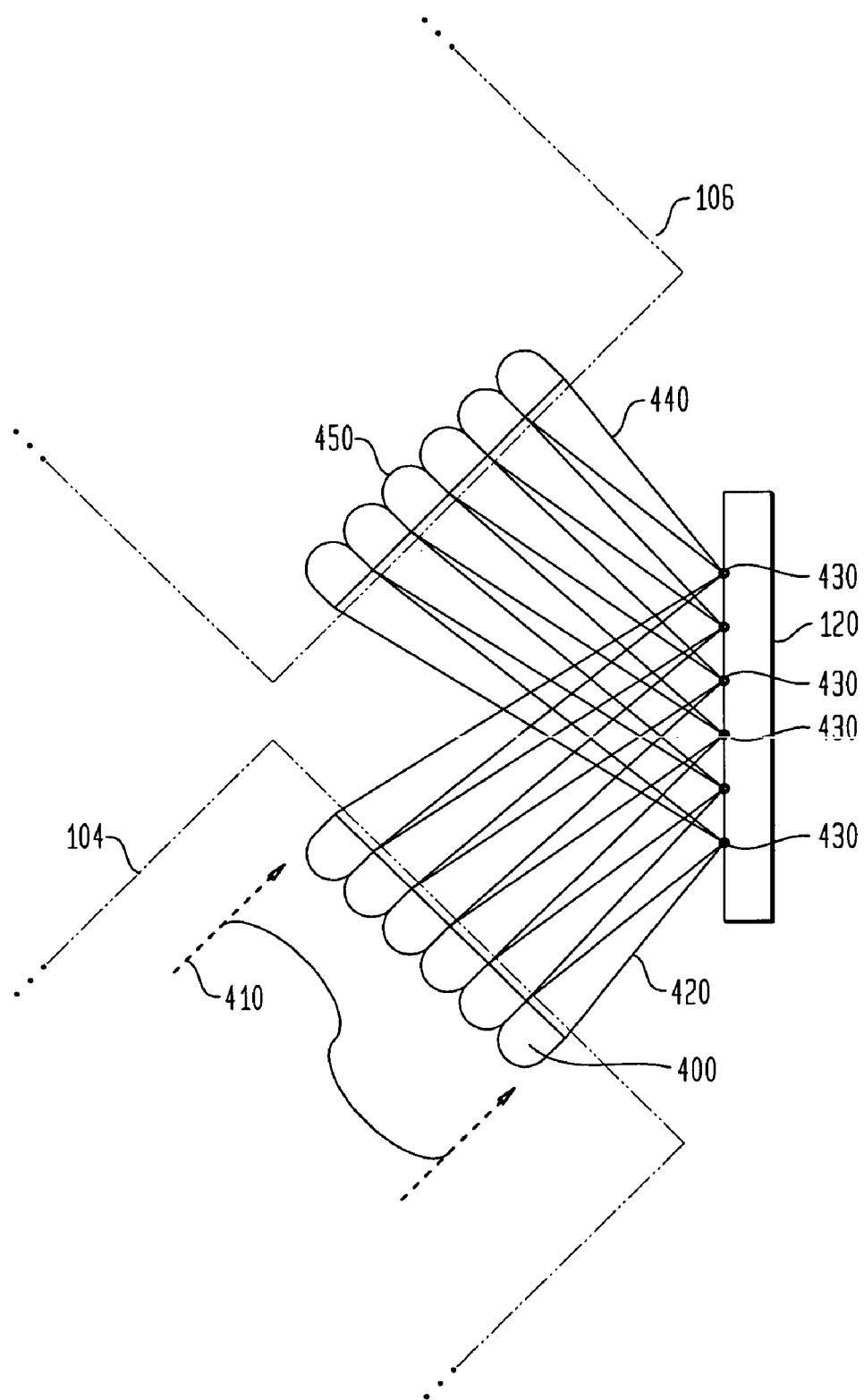
FIG. 4 is a diagram showing an example of a lenslet array that is incorporated into the apparatus of FIG. 1 in accordance with a still further aspect of the invention.

Alternatively, as FIG. 4 shows, a further lenslet array 450 is used in place of the lens 350 in the detection system. In the illumination system 106, the incoming light beam 410 is divided into a plurality of light rays 420 by a first lenslet array 400 of the illumination system 104 in the manner described above and directed onto a plurality of locations 430 on the surface of the substrate 120. The scattered or reflected rays 440 from the surface of the substrate are then directed into a further lenslet array 450 of the light detection system 106 for processing by further known measurement systems. The use of lenslet arrays as a sensor is known in the art, such as is used in a Shack-Hartmann sensor.

A detection system, such as is shown in FIGS. 3 or 4, may also be used in combination with the illumination arrangement shown in FIG. 2 but is disposed to receive light rays that are reflected or scattered off a substrate that is illuminated with normally incident light rays.

Figure 5:
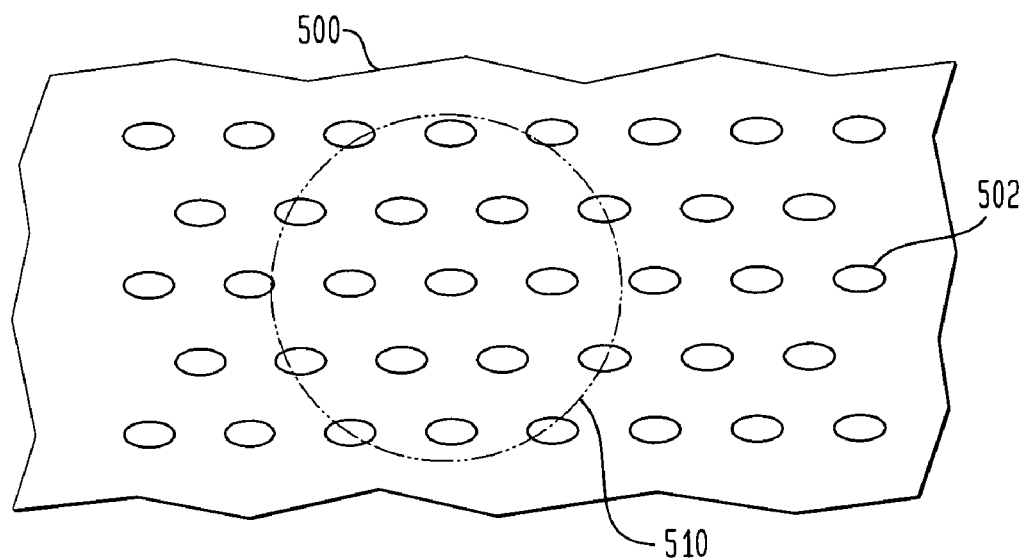
FIG. 5 is a diagram showing a known illumination pattern of a region of a wafer.

FIG. 5 illustrates an example of a substrate that is illuminated in a known manner. The substrate 500 includes a plurality of trenches 502. A circular region 510 of the substrate 500 is illuminated to permit a property of the trench located at the center of the region 510 to be measured. Because of the small size of the trenches 502, the trenches only occupy a small proportion of the total area illuminated, thereby increasing the noise present when the measurements are taken. The degraded signal-to-noise ratio reduces the sensitivity of the measurements.

The present invention improves the sensitivity of the measurements of the properties of features formed in a substrate by concentrating the light onto one or more regions of the substrate having dimensions that are much closer to those of the measured features. The amount of light that illuminates the background regions is significantly reduced so that the features of interest take up a much higher proportion of the illuminated area.

Figure 6:
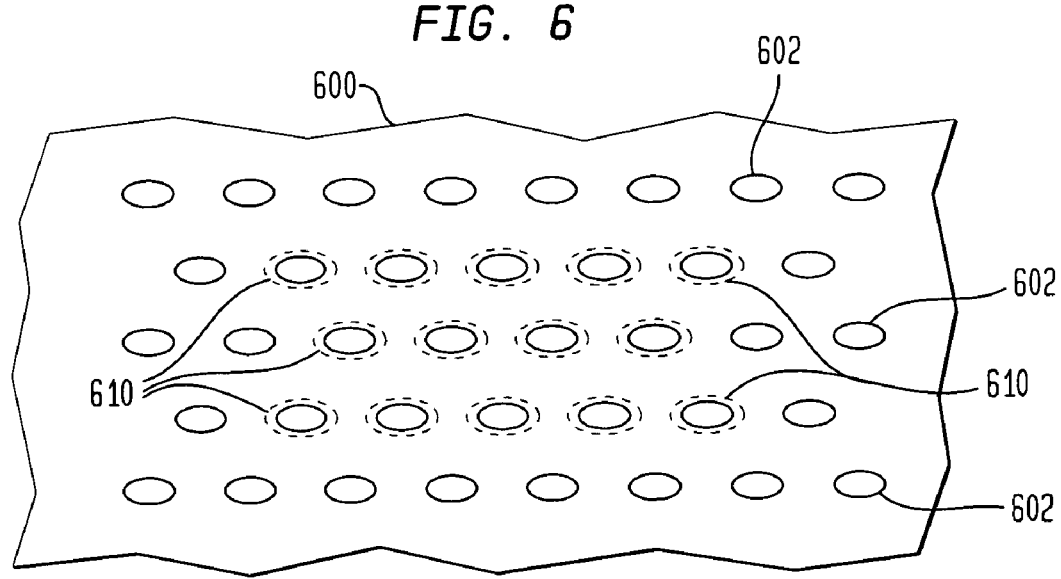
FIG. 6 is a diagram showing illumination patterns of a region of a wafer in accordance with the invention.

FIG. 6 illustrates an example of a region of a substrate 600 that is illuminated in accordance with an aspect of the invention. A plurality of trenches 602 are formed in the substrate 600. Small region 610 of the substrate 600 are illuminated using the lenslet array illumination system of the invention by arranging the optical elements of the illumination system to each focus on a respective trench of the trenches 402.

Generally, the spacing between adjacent features, such as the distance between the rows of trenches 602 or the distance between the individual trenches of a row of trenches, is known for a particular generation of devices based on the design rules of the photolithographic masks used to print the features. Because these distances are known, the diameter, spacing and angles of the lenslets of the lenslet array may be disposed so that each lenslet of the array illuminates a particular trench with only a minimum amount of "background" area being illuminated. Typically, the lenslet array is manufactured for a particular feature level and device generation, though a particular lenslet array may be suitable for more than one device levels, such as by adjusting the position and angle of the lenslet array.

Advantageously, the width of the region 610 is about the same or only slightly greater than the width of the trenches 602 so that the portion of the region 610 taken up by the trenches 602 is maximized. The light incident on the region 610 may be reflected or scattered by the features 602 within the region 610 so that a property of the trenches 602, such as the window width, profile, depth or sidewall angle may be measured.

Similarly, the invention is suitable for other types, of features, such as windows, vias or line features. When such features are illuminated in the manner of the invention, other properties, such as the width or height of line features or space features, the partial opening or closing of contact windows or vias, or the photolithographic level-to-photolithographic level overlay may be measured.

Additionally, the invention is suitable for various types of measurements such as for reflectometry measurements, scatterometry measurements, critical dimension measurements, etch control measurements, etc. The invention may be used to, for example, measure line widths, line spacings, sidewall angle and/or profile, trench depth, and the presence of open or partially opened windows and vias.

The present invention therefore provides for the illumination of the features of interest of a substrate in which the illuminated area is minimized. As a result, the quantity of noise in relation to the measurement signal is reduced, and the sensitivity of the measurement is increased.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of minimizing background illumination while illuminating features formed on a substrate, said method comprising:
   directing a light beam onto a lenslet array comprised of at least two lenslets; and
   dividing the light beam into at least two light rays and directing said at least two light rays from said lenslet array directly onto said substrate, said lenslet array having a focal plane substantially coincident with the surface of the substrate:
   said lenslets of said lenslet array each directing a respective one of said light rays onto a corresponding region of said substrate that includes a feature formed on substrate:
   said width of said region and said width of said feature being substantially equal.

2. The method of claim 1 further comprising measuring a property of said feature using light detected from said feature.

3. The method of claim 1 wherein adjacent ones of said light rays are directed by said lenslets of said lenslet array onto adjacent features formed on said substrate.

4. The method of claim 1 wherein said light rays are directed by said lenslets of said lenslet array onto said substrate at an angle normal to a surface of said substrate.

5. The method of claim 1 wherein said light rays are directed by said lenslets of said lenslet array onto said substrate at an oblique angle to a surface of said substrate.

6. A method of minimizing background illumination while illuminating features formed on a substrate, said method comprising:
   directing a light beam onto a lenslet array comprised of a plurality of lenslets; and
   dividing the light beam into a plurality of light rays and directing each of said plurality of light rays from said lenslet array directly onto said substrate, said lenslet array having a focal plane substantially coincident with the surface of said substrate;
   said lenslets of said lenslet array each directing a respective one of said light rays onto a corresponding region of said substrate that includes a feature formed on said substrate;
   adjacent lenslets of said lenslet array directing adjacent ones of said light rays onto adjacent features formed on said substrate and said width of said light rays and said width of said features being substantially equal.

7. The method of claim 6 further comprising measuring a property of said features using light detected from said features.

8. The method of claim 6 wherein said lenslet array comprises a two dimensional array of lenslets.

9. The method of claim 6 wherein said light rays are directed by said lenslets of said lenslet array onto said substrate at an angle normal to a surface of said substrate.

10. The method of claim 6 wherein said light rays are directed by said lenslets of said lenslet array onto said substrate at an oblique angle to a surface of said substrate.

11. The method of claim 6 wherein said light rays are focused by said lenslets of said lenslet array at said substrate.

12. A method of measuring a property of features formed on a substrate, said method comprising:
    directing a light beam onto a lenslet array comprised of at least two lenslets; and
    dividing the light beam into at least two light rays and directing said light rays from said lenslet array directly onto said substrate, said lenslet array having a focal plane substantially coincident with the surface of said substrate;
    measuring a property of at least one feature using light detected from said feature; and
    said lenslets of said lenslet array each directing a respective one of said light rays onto a corresponding region of said substrate that includes a feature formed on said substrate, and said width of each light rays and said width of said corresponding feature being substantially equal.

13. The method of claim 12 wherein said property is selected from the group consisting of: a line width, a line height, a sidewall angle, a sidewall profile, a trench depth, and a presence of an open or partially opened feature.

14. The method of claim 12 wherein said light detected from said feature is selected from the group consisting of: reflected light and scattered light.

15. The method of claim 12 wherein adjacent ones of said light rays are directed by said lenslets of said lenslet array onto adjacent features formed on said substrate.

16. The method of claim 12 wherein said lenslet array comprises a two dimensional array of lenslets.

17. The method of claim 12 wherein said light rays are directed by said lenslets of said lenslet array onto said substrate at an angle normal to a surface of said substrate.

18. The method of claim 12 wherein said light rays are directed by said lenslets of said lenslet array onto said substrate at an oblique angle to a surface of said substrate.

19. The method of claim 12 wherein said measuring step includes focusing said light detected from said features using a further lenslet array comprised of at least two further lenslets.

20. An apparatus for measuring a property of features formed on a substrate, said apparatus comprising:
    a light source;
    a target substrate having a surface;
    a lenslet array comprising at least two lenslets, said lenslets of said lenslet array for dividing an incident light beam from said source into at least two light rays having a focal plane substantially coincidental with said surface of said target substrate, said lenslets of said lenslet array each directing a respective one of said light rays onto a corresponding region of said substrate that includes a feature formed on said substrate said corresponding regions of said substrate illuminated by each light ray having a selected width substantially equal to said included feature; and a detection system operable to measure a property of said feature using light detected from said feature.

21. The apparatus of claim 20 wherein said property is selected from the group consisting of: a line width, a line height, a sidewall angle, a sidewall profile, a trench depth, and a presence of an open or partially opened feature.

22. The apparatus of claim 20 wherein said light detected from said feature is selected from the group consisting of: reflected light and scattered light.

23. The apparatus of claim 20 further comprising a control system operable to control an orientation of said lenslet array.

24. The apparatus of claim 20 further comprising a control system operable to process a measured value received from said detection system.

25. The apparatus of claim 20 wherein said lenslets of said lenslet array direct adjacent ones of said light rays are onto adjacent features formed on said substrate.

26. The apparatus of claim 20 wherein said lenslet array comprises a two dimensional array of lenslets.

27. The apparatus of claim 20 wherein said lenslets of said lenslet array direct said light rays onto said substrate at an angle normal to a surface of said substrate.

28. The apparatus of claim 20 wherein said lenslets of said lenslet array direct said light rays onto said substrate at an oblique angle to a surface of said substrate.

29. The apparatus of claim 20 wherein said lenslets of said lenslet array focus said light rays at said substrate.

30. The apparatus of claim 20 wherein said detection system includes a further lenslet array operable to focus said light detected from said features, said further lenslet array being comprised of at least two further lenslets.

* * * * *